United States Patent [19]

Katz

[11] Patent Number: 4,690,675
[45] Date of Patent: Sep. 1, 1987

[54] INTRAVENOUS NEEDLE ASSEMBLY

[76] Inventor: William Katz, 550 Parmalee Ave., Youngstown, Ohio 44510

[21] Appl. No.: 872,867

[22] Filed: Jun. 11, 1986

Related U.S. Application Data

[63] Continuation-in-part of Ser. No. 672,926, Nov. 19, 1984, Pat. No. 4,627,842.

[51] Int. Cl.$^4$ .............................................. A61M 5/32
[52] U.S. Cl. .................................... 604/177; 604/180; 128/DIG. 26
[58] Field of Search ............... 604/161, 164, 165, 169, 604/174, 177, 179, 186, 272; 128/133, DIG. 26, 340, DIG. 6

[56] References Cited

U.S. PATENT DOCUMENTS

| | | | |
|---|---|---|---|
| 2,402,306 | 6/1946 | Turkel | 128/DIG. 26 |
| 2,409,432 | 10/1946 | Hubbard | 604/179 |
| 2,525,398 | 10/1950 | Collins | 604/179 |
| 3,064,648 | 11/1962 | Turkel | 604/177 |
| 3,461,869 | 8/1969 | Hargest | 128/DIG. 26 |
| 4,250,880 | 2/1981 | Gordon | 604/180 |
| 4,366,817 | 1/1983 | Thomas | 604/174 |
| 4,380,234 | 4/1983 | Kamen | 604/180 |
| 4,392,856 | 7/1983 | Lichtenstein | 604/177 |
| 4,397,641 | 8/1983 | Jacobs | 128/DIG. 26 |
| 4,563,177 | 1/1986 | Kamen | 604/177 |
| 4,565,544 | 1/1986 | Muller et al. | 604/164 |

Primary Examiner—C. Fred Rosenbaum
Assistant Examiner—Jerome R. Smith, Jr.
Attorney, Agent, or Firm—Harpman & Harpman

[57] ABSTRACT

An intravenous needle assembly includes a hollow needle having a beveled point, the needle being positioned transversely of a central section of an elongated, flexible, foldable body having oppositely disposed wing sections. The needle is provided with a flexible connecting tube and a connector for attachment to a desired device, such as a syringe, bottle, etc. The central section mounting the needle and the oppositely disposed wing sections are tapered transversely with a pressure sensitive adhesive on the lower surface thereof for application to the skin of a patient's body. The needle is angled downwardly by the tapered structure when moved into the vein to position the beveled pointed end away from the walls of the vein.

3 Claims, 3 Drawing Figures

INTRAVENOUS NEEDLE ASSEMBLY

This is a continuation-in-part of Ser. No. 06/672,926 filed 11/19/84 and now U.S. Pat. No. 4,627,842.

BACKGROUND OF THE INVENTION

1. Technical Field

This invention relates to intravenous needle assemblies such as employed in infusion sets.

2. Description of the Prior Art

Prior devices of this type may be seen in U.S. Pat. Nos. 3,064,648, 4,250,880, and 4,380,234.

U.S. Pat. No. 3,064,648 discloses an intravenous needle assembly in which there are flat foldable wings on either side of the needle, the foldable wings begin defined by weakened portions adjacent to and parallel with the hollow needle. The present invention utilizes similarly formed foldable wings, but more importantly provides a tapered pad or elongated body member for positioning the needle at an angle with respect to the vein in which it is positioned.

The present invention has no comparable needle supporting or holding or positioning structure.

U.S. Pat. No. 4,250,880 positions a catheter hub in a cradle located between thin flat lateral wings which extend from the cradle. The wings are provided with adhesive surfaces for engagement with the patient's skin. The present invention differs in that a single pair of foldable wings are employed and provides a transversely tapered foamed body for tilting the needle relative to the patient's skin surface to advantageously position the open beveled end of the needle in the patient's vein.

U.S. Pat. No. 4,380,234 discloses a hollow needle positioned in a cylindrical holder angularly mounted in a circular disk clip. No similar construction is found in the present invention which provides a simple, inexpensive intravenous needle assembly which may be quickly and easily inserted in a patient's vein and adhesively attached to the patient's skin to automatically incline the needle relative to the patient's skin and vein so as to advantageously position the needle in the vein.

SUMMARY OF THE INVENTION

An intravenous needle assembly provides an elongated hollow needle with a beveled end forming a point mounted transversely of a flexible transversely tapered elongated distortable member having oppositely disposed outwardly extending foldable wings, the lower portions of which are provided with an adhesive surface. Flexible connecting tubing engages the needle and extends to a connecter. The transversely tapered member may be formed of a thin flat strip and a transversely tapered foam pad that will automatically position the needle in inclined relation to the patient's skin and the vein in which the needle is inserted to insure the positioning of the beveled open end of the needle in unencumbered relation to the walls of the vein.

DESCRIPTION OF THE PREFERRED EMBODIMENT

Figure 1:
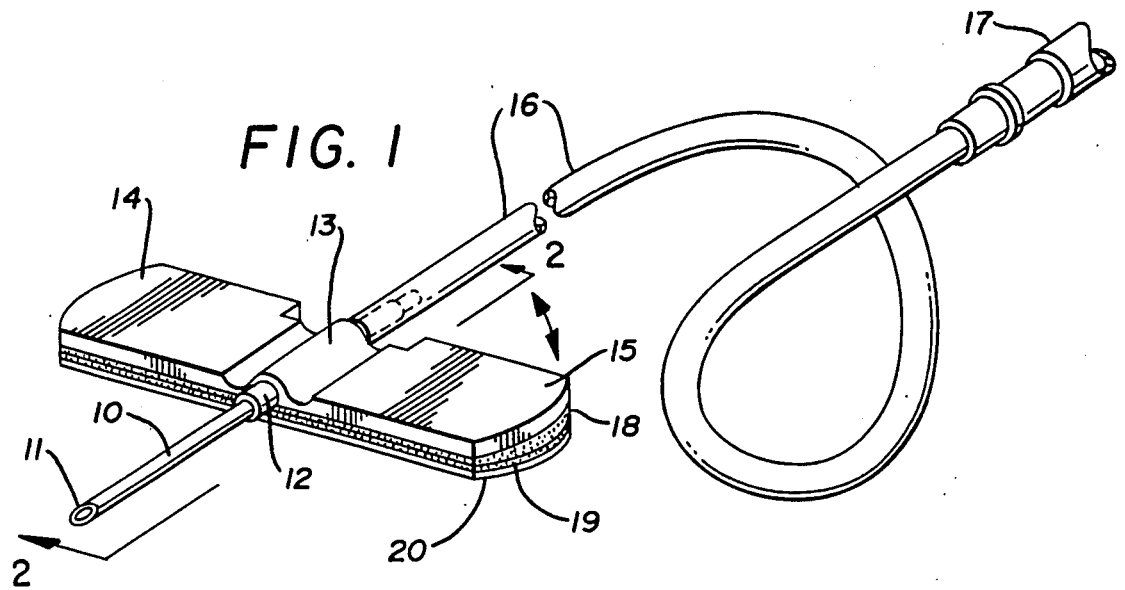
FIG. 1 is an enlarged perspective view of the intravenous needle assembly.

By referring to the drawings and FIG. 1 in particular, it will be seen that the intravenous needle assembly comprises a hollow needle 10 having a pointed end formed by a bevel 11. The hollow needle 10 is positioned in a cylindrical member 12 located transversely of a central body 13 having oppositely disposed outwardly extending wing sections 14 and 15 joined thereto. The central body 13 and the outwardly extending wing sections 14 and 15 are formed of flexible, distortable synthetic resin material so that the wing sections 14 and 15 may be grasped and moved upwardly toward one another where they will form a convenient handle for holding the needle 10 and inserting it in a patient's vein. The opposite end of the needle 10 with respect to the beveled point 11 extends outwardly of the central body 13 and preferably through an extension of the cylindrical member 12 and is secured to one end of a flexible connecting tube 16, the other end of which is provided with a connector 17 by means of which the intravenous needle assembly can be connected to an intravenous bottle, syringe, or the like.

Figure 2:
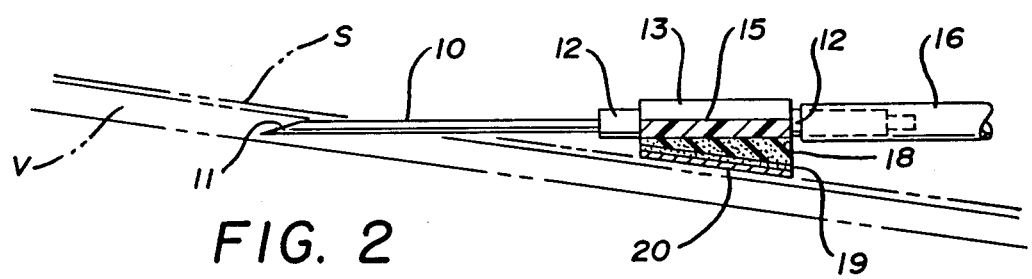
FIG. 2 is a cross section on line 2—2 of FIG. 1, broken lines indicating a skin surface and a vein outline in which the needle is positioned.

Still referring to FIGS. 1 and 2 of the drawings, it will be seen that a tapered pad 18 preferably formed of plastic foam or the like and tapered from one longitudinal edge to the other with its thinnest edge adjacent the side of the central body 13 and outwardly extending wings 14 and 15 from which the pointed end 11 of the hollow needle 10 extends and its thickest edge lying adjacent the opposite side of the central body 13 and the outwardly extending flexible wings 14 and 15 which is adjacent the flexible connecting tube 16.

A layer of pressure sensitive adhesive is positioned on the entire lower surface of the tapered pad 18 and is provided with a removable cover sheet 20.

Figure 3:
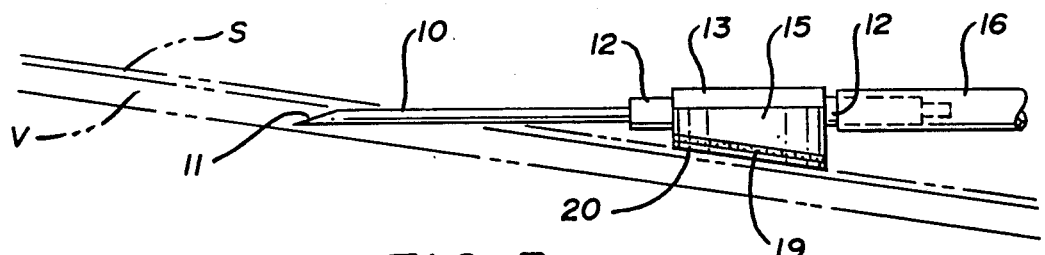
FIG. 3 is a side view of the needle assembly of FIG. 1, broken lines indicating a skin surface and a vein outline in which the needle is inserted.

Still referring to FIGS. 1 and 2 of the drawings, it will be seen that when the cover sheet 20 is removed from the adhesive 19, the oppositely disposed flexible wing sections 14 and 15 may be bent upwardly toward one another to form a convenient handle which may be grasped between the fingers of the physician or nurse positioning the needle assembly in a patient's vein and that when the needle is being positioned in the vein, the flexible wing sections upon being released will assume their normal oppositely disposed position due to the resiliency of the material of which they are formed whereupon they may be moved downwardly into contact with the skin of the patient to secure the intravenous needle assembly in desirable position and by referring to FIGS. 2 and 3 of the drawings, broken lines S and V will be seen to represent a patient's skin and vein in which the intravenous needle assembly has been positioned and it will be observed that the tapered pad 18 has positioned the hollow needle 10 at an angle of about 10° from the plane of the skin surface S and the vein V so that the beveled point 11 is positioned in the vein in spaced relation to the walls of the vein and is therefore unencumbered and permits ready flow of fluid into the vein or blood from the vein as desired.

A modification of the above-described invention may be formed by molding the flexible wing sections 14 and 15 and the central body 13 of the intravenous needle assembly of a resilient foamed plastic in an integral unit thereby combining the tapered pad 18 with the central body 13 and wing sections 14 and 15 which will have the same shape and appearance illustrated in FIG. 3 of the drawings.

It will thus be seen that an intravenous needle assembly has been disclosed which is inexpensive to manufacture, easy to use and automatically positions the needle at an angle to the surface of the patient's skin and the vein thereinunder in which the needle is positioned.

Having thus described my invention, what I claim is:

1. An improvement in an intravenous needle assembly having an elongated flexible body member with upper and lower surfaces with a central section and oppositely extending wing sections with respect thereto, and a hollow needle having a beveled end positioned through said central section transversely of said elongated flexible body member on a transverse horizontal plane; the improvement comprising means for tilting said elongated flexible body member and the hollow needle from said transverse horizontal plane to an angular transverse plane with respect to said transverse horizontal plane when said assembly is applied to a patient's skin, said means comprising at least one longitudinally extending transversely tapered resilient pad positioned on said elongated flexible body member in oppositely disposed relation to said central section and said hollow needle so that when said hollow needle of said assembly is positioned through a patient's skin and into a vein of said patient, said tapered flexible body member engages the patient'skin and tilts said central section and said hollow needle relative to said patient's skin and vein and spaces the beveled end of said hollow needle in unencumbered relation to the walls of said vein.

2. The improvement in an intravenous needle assembly set forth in claim 1 and wherein said angular transverse plane is located at about 10° from said transverse horizontal plane.

3. The improvement in an intravenous needle assembly set forth in claim 2 wherein pressure sensitive adhesive is located on said longitudinally extending, transversely tapered pad for holding said assembly in engagement with a patient's skin whereby said central section and said elongated flexible body member and said hollow needle are secured in angular relation to said patient's skin and said vein.

* * * * *